United States Patent
Williams

[19]

[11] Patent Number: 5,987,746
[45] Date of Patent: Nov. 23, 1999

[54] METHOD OF MAKING MEDICAL ELECTRICAL LEAD

[75] Inventor: Terrell M. Williams, Brooklyn Park, Minn.

[73] Assignee: Medtronic, Inc., Minneapolis, Minn.

[21] Appl. No.: 08/604,591

[22] Filed: Feb. 21, 1996

[51] Int. Cl.$^6$ .................................................. H01R 43/20
[52] U.S. Cl. .............................. 29/876; 29/825; 607/120
[58] Field of Search ....................... 29/825, 876; 607/120

[56] References Cited

U.S. PATENT DOCUMENTS

| | | |
|---|---|---|
| 4,506,680 | 3/1985 | Stokes . |
| 4,577,642 | 3/1986 | Stokes . |
| 4,711,251 | 12/1987 | Stokes . |
| 4,819,662 | 4/1989 | Heil, Jr. et al. . |
| 4,866,051 | 9/1989 | Hunt et al. ............................ 514/180 |
| 4,972,848 | 11/1990 | Di Domenico et al. . |
| 5,103,837 | 4/1992 | Weidlich et al. ....................... 128/784 |
| 5,208,226 | 5/1993 | Palmer . |
| 5,246,014 | 9/1993 | Williams et al. . |
| 5,282,844 | 2/1994 | Stokes et al. . |
| 5,324,324 | 6/1994 | Vachon et al. . |
| 5,324,325 | 6/1994 | Moaddeb . |
| 5,408,744 | 4/1995 | Gates . |
| 5,443,492 | 8/1995 | Stokes et al. . |

FOREIGN PATENT DOCUMENTS

| | | |
|---|---|---|
| 0 388 480 A1 | 3/1989 | European Pat. Off. . |
| 0 622 090 A1 | 4/1994 | European Pat. Off. . |

OTHER PUBLICATIONS

"Immunosuppression by Glucocorticoids: Inhibition of NF-$_K$B Activity Through Induction of I$_K$B Synthesis" by Auphan et al, Science, vol. 270, Oct. 13, 1995.

"How the Glucocorticoids Suppress Immunity" by Jean Marx, Science, vol. 270, Oct. 13, 1995.

"Role of Transcriptional Activation of I$_K$B$_A$ in Mediation of Immunosuppression of Glucocorticoids" by Robert I. Scheinman et al., Science, vol. 270, Oct. 13, 1995.

*Primary Examiner*—Carl J. Arbes
*Attorney, Agent, or Firm*—Thomas F. Woods; Harold Patton; Michael J. Jaro

[57] ABSTRACT

A medical electrical lead having a drug which is no more than sparingly soluble in water applied to the electrode surface. In the preferred embodiment the lead of the present invention possesses an electrode treated with a very slightly soluble in water steroid, such as beclomethasone dipropionate anhydrous. Preferably the steroid is applied to the surface of the electrode which contacts tissue when implanted. A method of manufacturing such a lead is also disclosed. Through such a design, a high impedance, low threshold lead which is simple and easy to manufacture is disclosed.

16 Claims, 5 Drawing Sheets

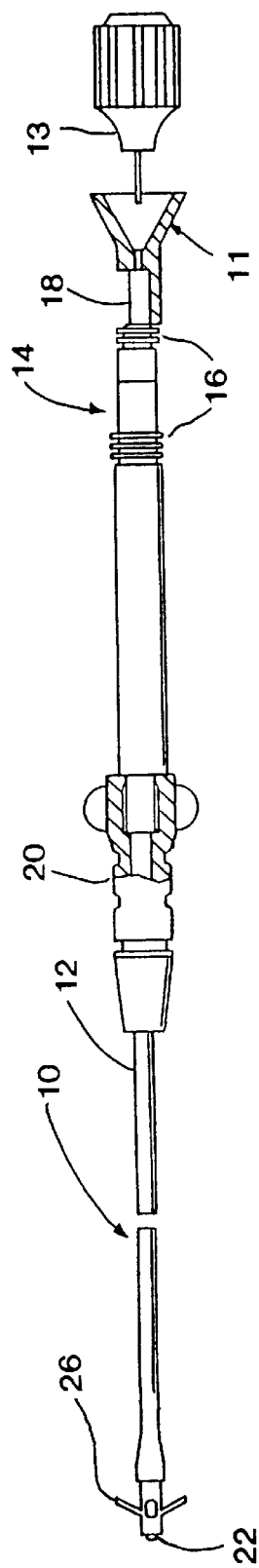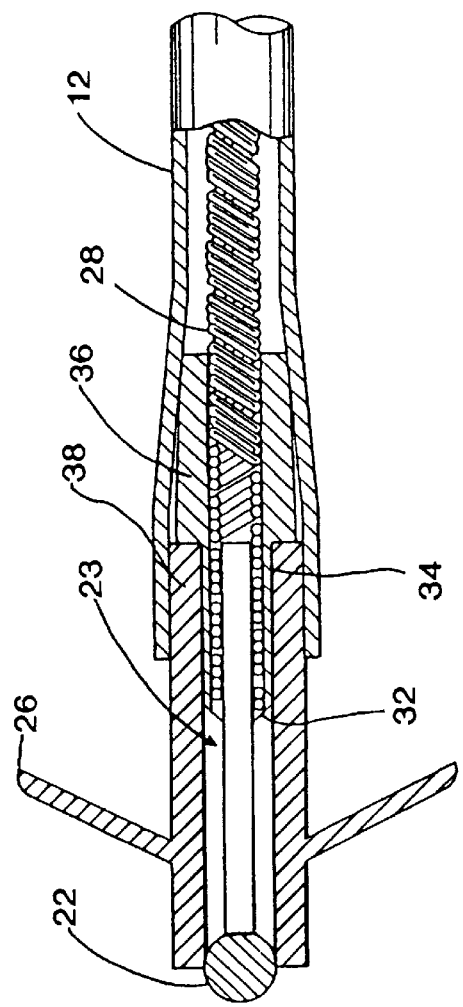
FIG. 1
FIG. 2

METHOD OF MAKING MEDICAL ELECTRICAL LEAD

BACKGROUND OF THE INVENTION

1. Field of the Invention

This invention relates generally to chronically implanted medical electrical leads and, in particular, to cardiac pacing leads which feature a drug which is no more than sparingly soluble in water applied to the electrode surface, e.g. beclomethasone dipropionate anhydrous.

2. Description of the Prior Art

Electrical stimulation of body tissue and organs is often used as a method of treating various pathological conditions. Such stimulation generally entails making an electrical contact between body tissue and an electrical pulse generator through use of one or more stimulation leads. Various lead structures and various techniques for implanting these lead structures into body tissue and particularly the heart have been developed.

For example, a transvenous endocardial lead establishes electrical contact between an electrical pulse generator and heart through placement of a lead in the venous system. Specifically, a transvenous endocardial lead is passed through a vein, with the assistance of a fluoroscope, into the heart where it may be held in contact with the endocardium by the trabeculae of the heart chamber, such as the ventricle. The safety, efficacy and longevity of an electrical pulse generator depends, in part, on the performance of its pacing lead(s).

During the past thirty years, there has been extensive research and development expended to optimize the performance of pacing leads and their reliability. In the early days of cardiac pacing, very high geometric surface area electrodes were employed with bulky and short-lived pacemaker pulse generators. Early investigators, such as Dr. Victor Parsonnet, advanced designs of pacing electrodes for achievement of low polarization and low thresholds while presenting a relatively small effective surface area for the delivery of a stimulating impulse in designs known as differential current density (DCD) of the type shown in U.S. Pat. No. 3,476,116. The DCD electrode (like all pacing electrodes of that time) suffered excessive chronic tissue inflammation and instability and was not pursued commercially.

Subsequent researchers, including Dr. Werner Irnich, explored in considerable detail the electrode-tissue interface and sought to arrive at an optimum exposed electrode surface area for both stimulation thresholds and sensing. See, for example Dr. Irnich, "Considerations in Electrode Design For Permanent Pacing" published in Cardiac Pacing; Proceedings of the Fourth International Symposium of Cardiac Pacing (H. J. Thalen, Ed.) 1973, pages 268–274.

Dr. Seymour Furman also studied the relationship of electrode size and efficiency for cardiac stimulation and presented a ball-tip/exposed spaced coil electrode and a small hemispheric electrode in his article entitled "Decreasing Electrode Size and Increasing Efficiency of Cardiac Stimulation" in Journal of Surgical Research, Volume 11 Number 3, Mar., 1971, pages 105–110. Dr. Furman concluded the practical lower limit of electrode surface area was in the range of 8 sq. mm, observing that impedance increased as an inverse function of the surface area.

Electrodes of many shapes including cylindrical, ball-tip, corkscrew, ring tip and open cage or "bird cage" configurations were pursued with exposed electrode surface areas tending toward 8 sq. mm in the mid 1970's.

More recently, various investigators have emphasized materials and their relationship to the considerations involved in optimizing electrode design. For example, the Medtronic U.S. Pat. No. 4,502,492 discloses a low polarization, low threshold electrode design of the early to mid 1980's which was commercialized as the "Target Tip"® pacing leads in numerous models including Models 4011, 4012, 4511 and 4512. The tip electrode of the Target Tip lead was generally hemispherical and provided with circular grooves. The electrode was fabricated of a platinum alloy, coated over its external surface with a plating of platinum black. The combination of the relatively low electrode surface area and platinum black contributed to state-of-the-art thresholds in that time period. Other manufacturers marketed porous platinum mesh (Cardiac Pacemakers, Inc.), totally porous sintered (Cordis Corporation), glassy and vitreous carbons (Siemens), and laser drilled metal (Telectronics Ppty. Ltd.) electrodes in that same time period.

A considerable breakthrough in the development of low threshold electrode technology occurred with the invention of the steroid eluting porous pacing electrode of Stokes U.S. Pat. No. 4,506,680 and related Medtronic U.S. Pat. Nos. 4,577,642, 4,606,118 and 4,711,281, all incorporated herein by reference. The electrode disclosed in the '680 patent was constructed of porous, sintered platinum or titanium, although carbon and ceramic compositions were mentioned. Within the electrode, a plug of silicone rubber impregnated with the sodium salt of dexamethasone phosphate or a water soluble form of other glucocorticosteroids was placed in a chamber. The silicone rubber plug allowed the release of the steroid through the interstitial gaps in the porous sintered metal electrode to reach into the tissue and prevent or reduce inflammation, irritability and subsequent excess fibrosis of the tissue adjacent to the electrode itself.

In particular, the steroid is believed to act upon and inhibit the inflammatory response of the body. The presence of the electrode, an object foreign to the body, activates macrophages. This occurs approximately three days after implant. Once activated the macrophages attach themselves to the surface of the electrode and form multi-nucleated giant cells. These cells, in turn, secrete various substances, such a hydrogen peroxide as well as various enzymes, in an effort to dissolve the foreign object. Such substances, while intending to dissolve the foreign object, also inflict damage to the surrounding tissue. When the surrounding tissue is the myocardium, these substance cause necrosis. These areas of necrosis, in turn, cause the electrical characteristics of the electrode tissue interface to degrade. Consequently pacing thresholds rise. Even after the microscopic areas of tissue die the inflammatory response continues and approximately seven days after implant the multi-nucleated giant cells cause fibroblasts to begin laying down collagen to replace the necrosed myocardium. This continues until completed and the electrode is encapsulated by a thick layer of fibrotic tissue, approximately twenty-eight days after implant. Typically the inflammatory response ends at this time.

Steroid, it is believed, inhibits the inflammatory response by inhibiting the activation of the macrophages. Because they do not form multi-nucleated giant cells, the subsequent release of substances to dissolve the object and which also destroy the surrounding tissue is prevented. Thus the necrosis of any tissue by the inflammatory response is minimized as well as the formation of the fibrotic capsule. Minimizing each of these reactions also minimizes the concomitant deterioration of the electrical characteristics of the electrode-tissue interface.

Thus, the incorporation of steroid elution permitted pacing leads to have a source impedance substantially lower as compared to leads featuring similarly sized solid electrodes. Leads which elute steroid also presented significantly lower peak and chronic pacing thresholds than similarly sized solid or porous electrodes.

One example of a lead which eluted steroid meeting widespread commercial success is the Medtronic Model 5534 CAPSURE Z™ lead. In particular this lead features an electrode with an exposed geometric surface area in the range of 0.1–4.0 sq. mm, preferably between 0.6 and 3.0 sq. mm, with about 1.0 sq. mm providing optimum performance. The lead had a pacing impedance of 1400+/−260 ohms and a source impedance of about 1650+/−410 ohms in both chambers of the heart. The electrode was hemispherical as exposed to the tissue and had a diameter of approximately 1 millimeter. The electrode was further fabricated of platinized porous platinum (or other porous electrode material) and required an annular shaped monolithic controlled release device (MCRD) loaded with an anti-inflammatory agent soluble with water which would then elute out of the lead and into the surrounding tissue, e.g., the steroid dexamethasone sodium phosphate. This water soluble steroid also was deposited within the pores of the porous platinum electrode.

Incorporating steroid so that it will elute from a lead, however, dramatically increased the relative complexity of lead construction, especially as compared to past, non-steroid eluting leads. For example, leads which elute steroid typically require an MCRD to contain the steroid and to thereafter slowly leach out the water soluble steroid into the surrounding tissue. Typically MCRDs were constructed from silicone rubber. Steroid eluting leads also required an area near the electrode in which to house the MCRD, as well as a high degree of dimensional control over the electrode in order to ensure proper steroid elution. Moreover, because steroids which elute within the body, such as the sodium salt of dexamethasone phosphate, often degrade at high temperatures, thermal processing during the production of a steroid eluting lead was not allowed once the MCRD was installed. Setting aside a volume near the electrode tip to house the MCRD, however, also tended to increase lead body stiffness in that area.

SUMMARY OF THE INVENTION

It is thus an object of the present invention to provide a high impedance, low threshold lead which is simple and easy to manufacture.

It is a further object of the present invention to provide a high impedance, low threshold lead which has the performance enhancements of steroid but which does not require an MCRD.

Briefly, the above and further objects and features of the present invention are realized by providing a medical electrical lead having a drug which is no more than sparingly soluble in water applied to the electrode surface. In the preferred embodiment the lead of the present invention possesses an electrode treated with a very slightly soluble in water steroid, such as beclomethasone dipropionate anhydrous. Preferably the steroid is applied to the surface of the electrode which contacts tissue when implanted. A method of manufacturing such a lead is also disclosed. Through such a design, a high impedance, low threshold lead which is simple and easy to manufacture is disclosed.

BRIEF DESCRIPTION OF THE DRAWINGS

The above and other options, features and advantages of the present invention will be more apparent from the following more particular description thereof, presented in conjunction with accompanying drawings, wherein:

FIG. 1 shows a side plan view of an endocardial, unipolar, ball-tip electrode pacing lead according to the present invention.

FIG. 2 shows a cross-sectional view of the ball-tip electrode of the lead shown in FIG. 1.

Figure 3:
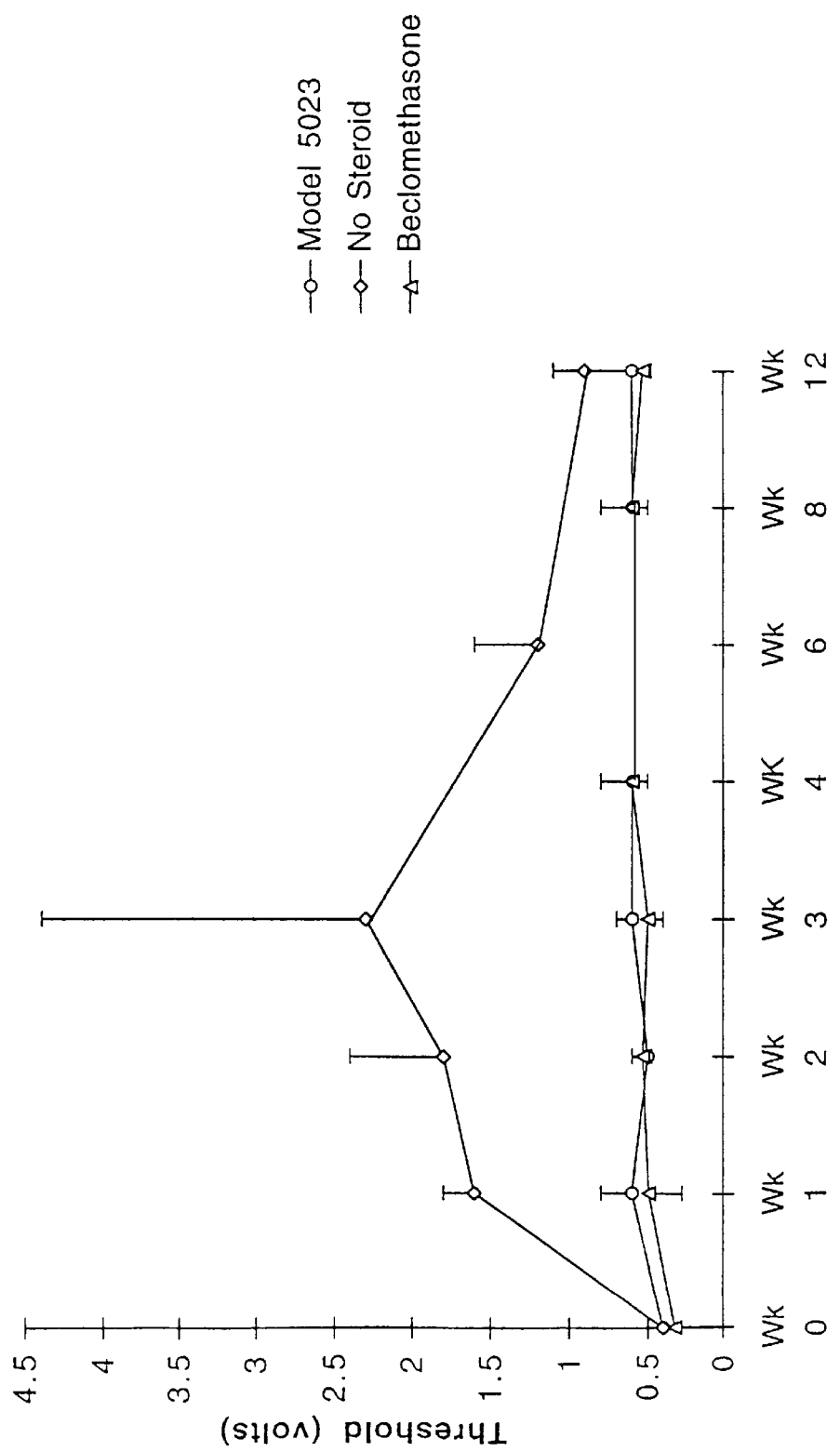
FIG. 3 depicts graphically the performance of the exposed electrodes of the present invention with steroid elution against electrodes of the same size and configuration without steroid elution.

The drawings are not necessarily to scale.

DETAILED DESCRIPTION OF THE DRAWINGS

For the purposes of this specification and claims, the term "lead" is used herein in its broadest sense and includes a stimulation lead, a sensing lead, a combination thereof or any other elongated member, such as a catheter, which may usefully be introduced into a body.

FIG. 1 illustrates a plan view of an exposed electrode constructed in accordance with the present invention. The lead includes an elongated lead body 10 covered by an insulative sleeve 12. Insulative sleeve 12 may be fabricated of any flexible biocompatible and biostable insulator especially silicone rubber or polyurethane. At the proximal end of the lead, terminal assembly 14 is adapted to couple the lead to an implantable pacemaker pulse generator. Terminal assembly 14 is provided with sealing rings 16 and a terminal pin 18, all of a type known in the art. An anchoring sleeve 20 (shown partially in cross-section) slides over lead body 10 and serves as a point for suturing the lead body to body tissue at the insertion point of the lead into the vein or tissue in a fashion known in the art. Anchoring sleeve 20 and terminal assembly 14 may be conveniently fabricated of silicone rubber.

The lead shown in FIG. 1 further includes a stylet guide 11 and stylet assembly 13 coupled to the terminal pin 18 for imparting stiffness to the lead during the insertion and placement of the lead transvenously into either the right ventricle or the right atrium of the heart. The stylet guide and stylet assembly are discarded after use and before connection of the terminal pin 18 to a pacemaker pulse generator. Distal end of the lead 10 features tines 26 to passively retain the tip electrode 22 in position against the endocardium as is well known in the pacing art.

The lead assembly 10 of FIG. 1 includes a multifilar conductor coil extending from the terminal pin 18 to the tip electrode 22. FIG. 1 depicts a unipolar lead and it should be understood that the present invention may be implemented in a bipolar lead design employing a second conductor extending from a second exposed cylindrical terminal surface area near the proximal end of the lead to an exposed ring electrode spaced from the distal tip electrode 22 as is well known in the art.

Referring now to FIG. 2, it shows in cross section a view of the distal lead portion of the preferred embodiment of the electrode of the present invention and its connection to the lead conductor 28. In FIG. 2, the distal electrode 22 is depicted as a porous platinum ball covered with platinum black at the end of a metal pin 23 of platinum alloy extending from the tip electrode 22 to the distal end of the conductor coil 28. Such a construction provides an electrode which with a high microscopic surface area in proportion to macroscopic surface area. While platinum is the preferred material, the electrode may also be used formed of porous metallic or other conductive materials from the class of materials consisting essentially of platinum, palladium, titanium, tantalum, rhodium, iridium, carbon, vitreous carbon and alloys, oxides and nitrides of such metals or other conductive materials. As seen distal electrode 22 preferably presents a generally hemispherical shape to any body tissue which would contact it after implantation. Distal electrode 22 preferably has a macroscopic surface area of less than 4.0 sq. mm. exposed to any body tissue which would contact it after implantation. The conductor coil 28 is attached to the proximal end of terminal pin 18 by crimping at point 34 of crimping member 36 at the time of manufacture. Silicone adhesive may be used at point 32 to seal the assembly against leakage of blood into the conductor coil. The insulative sheath 12 is shown placed over the crimping member as well as the tine assembly 38 which is fit between the distal end of the insulative sheath 12 and the crimping member 36.

As discussed above, tip electrode 22 is treated with a steroid which is non-elutable in the human body. This is accomplished through a steroid which has much less solubility in water as compared to the steroids used in the prior art steroid eluting pacing leads. In the preferred embodiment the steroid is beclomethasone dipropionate anhydrous, although other forms of drugs or steroids may also be used, including those which are sparingly soluble in water, slightly soluble in water, very slightly soluble in water, and practically insoluble in water or insoluble in water. Beclomethasone dipropionate anhydrous, for example, is very slightly soluble in water, very soluble in chloroform, or freely soluble in acetone and in alcohol. These descriptions of solubility are well known in the art and are used according to the following, well understood, definitions:

| Descriptive Term | Parts of Solvent Required for 1 Part Solute |
| --- | --- |
| Very Soluble | Less than 1 |
| Freely Soluble | From 1 to 10 |
| Soluble | From 10 to 30 |
| Sparingly Soluble | From 30 to 100 |
| Slightly Soluble | From 100 to 1000 |
| Very Slightly Soluble | From 1000 to 10,000 |
| Practically Insoluble, or Insoluble | 10,000 and over |

In regard to exposed electrodes of the present invention featuring a very slightly soluble in water steroid and those featuring steroid elution as compared to those electrodes without any steroid, the difference in stimulation thresholds is striking. FIG. 3 depicts the graphed results of a comparative study in canines of ventricular leads with and without steroid over an 12 week study period. The stimulation thresholds show a marked rise for the leads without steroid as compared to those leads with either a very slightly soluble in water steroid or steroid elution. Of course, the steroid eluting lead, as discussed above, is more complicated to manufacture. Thus, this FIG. 3 represents an important advantage over the present invention as compared to prior art leads. That is, the present invention offers the performance of a steroid eluting lead (which requires an MCRD) with a lead which does not require an MCRD. As such the present invention provides a high performance lead which is much less complicated to manufacture as compared to past lead designs.

Figure 4:
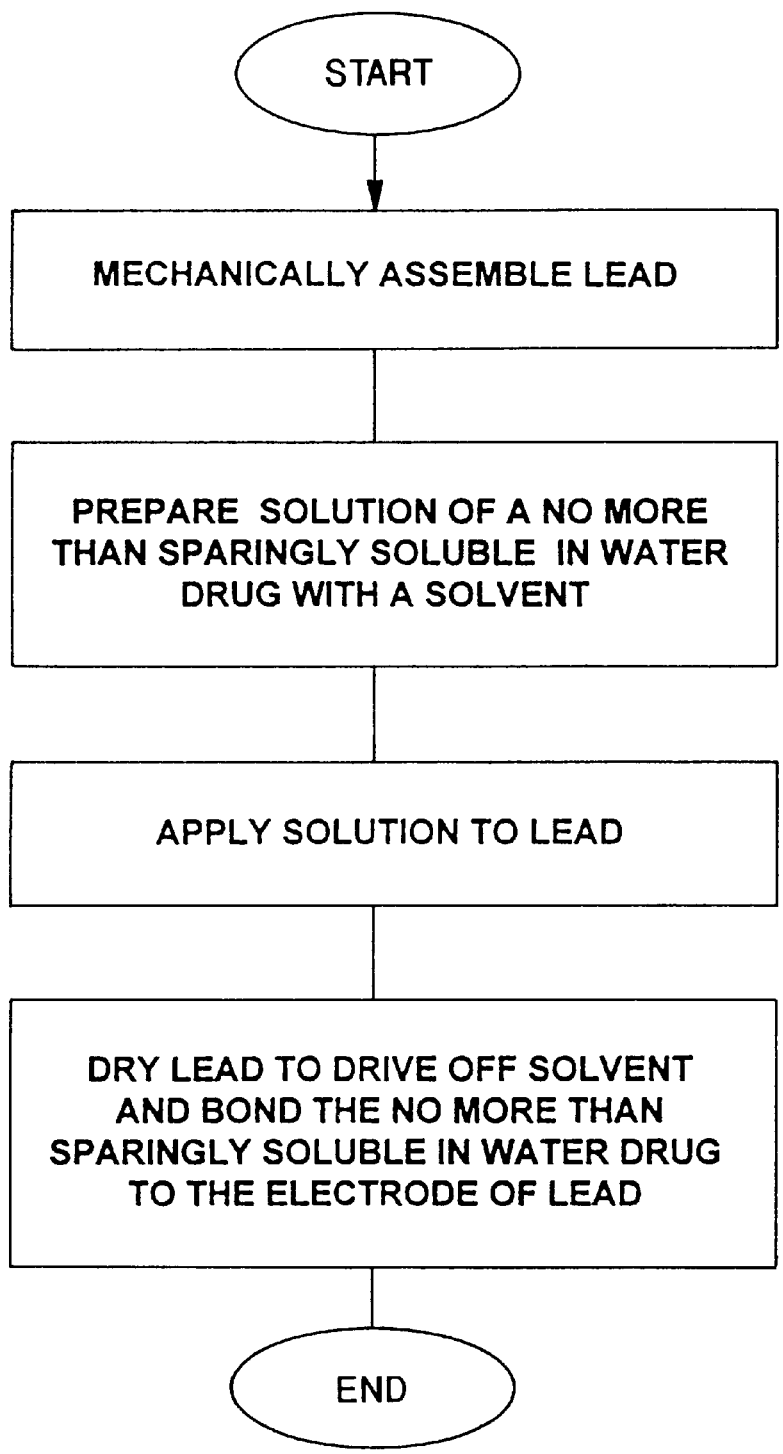
FIG. 4 depicts the steps employed in the manufacture of such a lead.

FIG. 4 is flowchart representing the salient steps of this method of manufacturing a medical electrical lead shown in FIGS. 1 and 2 . As seen, the method of manufacturing consists essentially of four stages: First the lead is mechanically assembled. This may be accomplished in any acceptable manner.

Next a solution of a no more than sparingly soluble in water drug with a solvent is prepared. In the preferred embodiment a saturated solution is used. This solution is prepared using the steps of dissolving beclomethasone dipropionate anhydrous micronized into acetone until a saturated solution is formed. A suitable beclomethasone dipropionate anhydrous micronized is available from Sicor S.P.A., 20017 Rho Milano, Via Terrazzano 77, Italy. A saturated solution is recognized when additional amounts of powdered beclomethasone dipropionate anhydrous do not dissolve, but rather merely falls to the bottom of the container. A suitable acetone meets American Chemical Society specifications and is available from Fisher Scientific, 711 Forbes Avenue, Pittsburgh, Pa. 15219-4785.

In an alternate embodiment of the present invention a saturated solution of a no more than sparingly soluble in water drug with a solvent may be prepared using the steroid betamethasone benzoate mixed with methanol. Once prepared, such a saturated solution is applied and dried to the electrode in the same manner as discussed below. A suitable methanol meets American Chemical Society specifications and is also available from Fisher Scientific, 711 Forbes Avenue, Pittsburgh, Pa. 15219-4785.

In a further alternate embodiment of the present invention a saturated solution of a no more than sparingly soluble in water drug with a solvent may be prepared using the steroid halcinonide mixed with chloroform. Once prepared, such a saturated solution is applied and dried to the electrode in the same manner as discussed below. A suitable halcinonide may be purchased from Westwood-Squibb Pharmaceuticals Inc., 100 Forest Ave. Buffalo, N.Y., 14213. A suitable chloroform meets American Chemical Society specifications and is also available from Fisher Scientific, 711 Forbes Avenue, Pittsburgh, Pa. 15219-4785.

In a further alternate embodiment of the present invention a saturated solution of a no more than sparingly soluble in water drug with a solvent may be prepared using the steroid diflorasone diacetate mixed with methanol. Once prepared, such a saturated solution is applied and dried to the electrode in the same manner as discussed below. A suitable diflorasone diacetate may be purchased from Dermik Laboratories Inc., 500 Arcola Rd., P.O. Box 1200, Collegeville, Pa., 19426-0107.

Of course, other organic solvents as well as other drugs which are no more than sparingly soluble in water may be used as well as other steroids, such as dexamethasone dipropionate anhydrous or any other drugs which are no more than sparingly soluble in water. In addition, although a saturated solution of the very slightly soluble in water drug and solvent is preferred, other solutions which are less than saturated may also be used.

Figure 5:
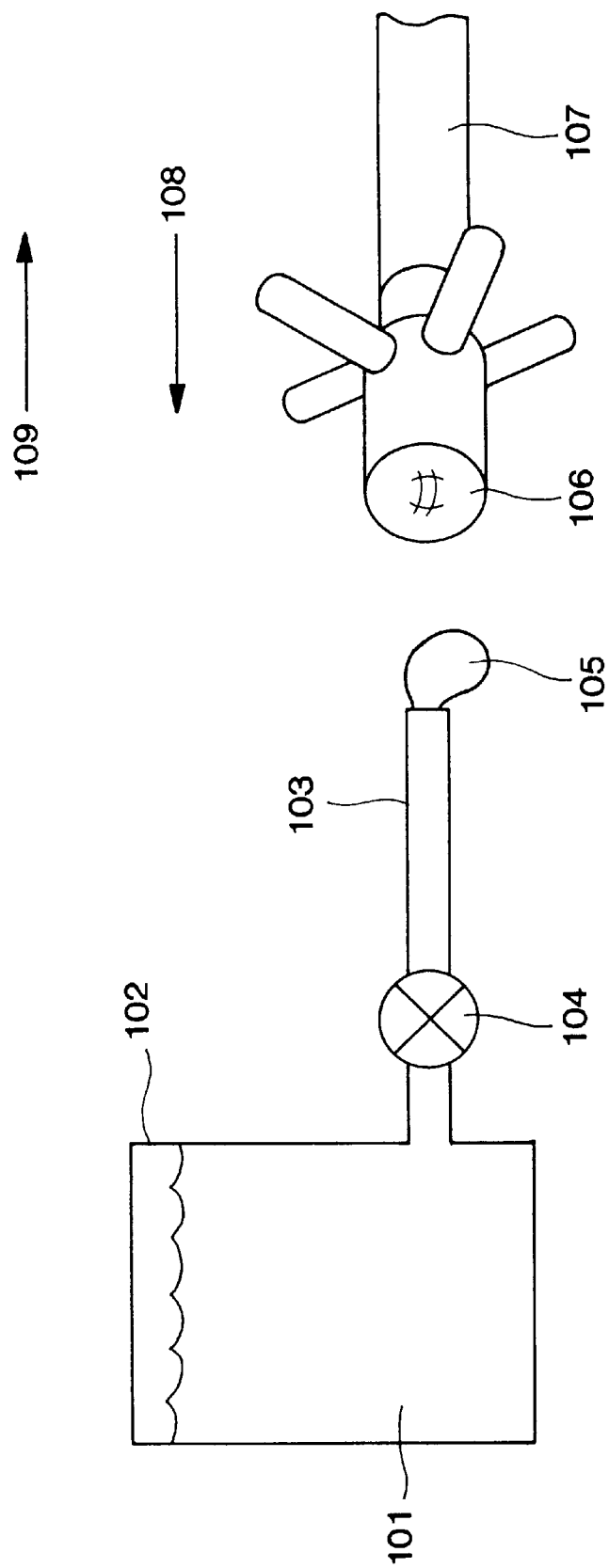
FIG. 5 shows an arrangement used to place a saturated solution of a very slightly soluble in water drug onto a lead.

Once an acceptable solution is prepared it is applied to the electrode on the lead, discussed in detail below in FIG. 5.

Finally, after the solution is applied, the electrode is dried to drive off the solvent and bond the no more than sparingly soluble in water drug to the electrode. Drying may be accomplished by allowing the solvent to evaporate at room temperature, although other methods may also be used. Once dried, a layer of the drug remains upon the surface of the electrode, as well as within its pores.

As mentioned above, FIG. 5 depicts a device used to apply the saturated solution of no more than sparingly soluble in water drug to an electrode. As seen the no more than sparingly soluble in water drug 101 is held within container 102, typically a motorized syringe. Container 102 has spigot 103, the flow through which is controlled by pump 104. Pump 104 is metered to permit only droplet 105 of no more than sparingly soluble in water drug 101 to a sufficient amount to wet onto electrode 106 of lead 107. In particular, once droplet 105 is formed off spigot 103, then lead 107 is moved in the direction 108. Once droplet 105 has been transported to electrode 106 then lead 107 is moved in the opposite direction 109.

As discussed above, once the saturated solution of the no more than sparingly soluble in water drug has been applied to the electrode it is dried.

One important characteristic offered by the use of a no more than sparingly soluble in water drug, and in particular by beclomethasone dipropionate anhydrous, is that the electrode surface is substantially encapsulated by the drug. An illustration of this is seen in FIG. 6.

Figure 6:
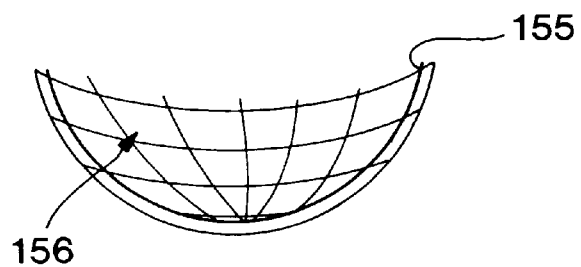
FIG. 6 shows a detailed side view of a pacing electrode which has had a saturated solution of a very slightly soluble in water steroid, such as beclomethasone dipropionate anhydrous, applied to its surface and dried.

FIG. 6 shows a detailed side view of a pacing electrode 155 which has had a saturated solution of acetone and a no more than sparingly soluble in water drug, such as beclomethasone dipropionate anhydrous, applied to its surface and dried. As seen, after the saturated solution is applied to the electrode surface and dried, a relatively uniform coating or layer 156 of the steroid is deposited over the entire surface. It is believed that the combination of the widespread presence of steroid at the surface where the electrode contacts tissue, along with its relative insolubility in water, causes the steroid to remain engaging with the tissue interface for a longer period of time. In addition, because only the tissue which contacts the electrodes gives rise to the inflammatory effect, steroid is only presented in the area in which it has effect.

Figure 7:
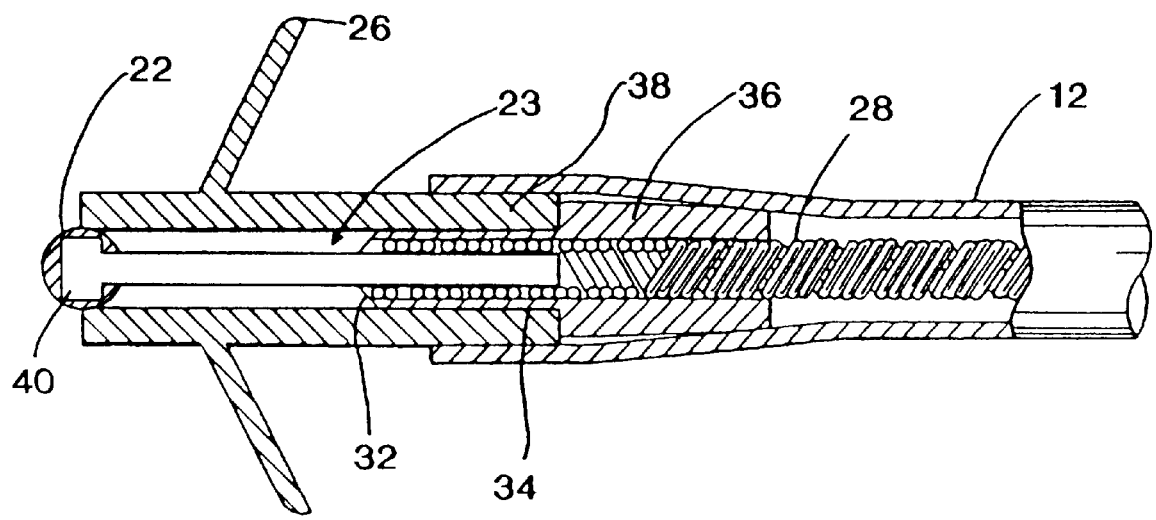
FIG. 7 shows an alternate embodiment of a ball-tip electrode featuring a stem having a nail-head shape.

FIG. 7 shows in cross section a view of the distal lead portion of an alternate embodiment ball-tip electrode of the present invention. As seen this embodiment is substantially similar to that shown in FIGS. 1 and 2 and thus the same numbers correspond to the same elements. As seen distal electrode 22 is a porous platinum ball covered with platinum black at the end of a metal pin 23 of platinum extending from the tip electrode 22 to the distal end of the conductor coil 28. Metal pin 23, as seen, differs from that disclosed in FIGS. 1 and 2 in that it features a nail-head shaped end 40. As discussed more fully in the U.S. Pat. No. 5,408,744 of Gates, incorporated herein by reference, such a shaped pin provides for a stronger electrode construction with enhanced impedance. The conductor coil 28 is attached to the proximal end of the pin by crimping at point 34 of crimping member 36. Silicone adhesive may be used at point 32 to seal the assembly against leakage of blood into the conductor coil. The insulative sheath 12 is shown placed over the crimping member as well as the tine assembly 38 which is fit between the distal end of the insulative sheath 12 and the crimping member 36. Like the previous embodiment discussed above, tip electrode 22 is treated with a saturated solution of a no more than sparingly soluble in water drug, and in particular with a very slightly soluble in water steroid, such as beclomethasone dipropionate anhydrous, in acetone. Of course although other forms of a very slightly soluble in water steroid may also be used.

While the embodiments of the present invention have been described in particular application to cardiac stimulation, the present invention may also be practiced in other electrode technologies where the aforementioned characteristics are desirable, including neurological and muscle stimulation applications, as well as other forms of treating or electrically stimulating other body tissues or organs.

In addition, although the preferred embodiment of the present invention features no more than sparingly soluble in water steroid applied to either the surface of an electrode or within the interstices of a porous electrode or both, the invention may utilize any anti-inflammatory agent or drug which is no more than sparingly soluble in water, including other types of steroid or drugs, including those which are sparingly soluble in water (e.g. medrysone), slightly soluble in water, very slightly soluble in water (e.g. desoximetasone, or triamcinolone), and practically insoluble in water or insoluble in water (e.g. fluoromethalone, flurandrenolide, halcinonide, desoximetasone, betamethasone benzoate, triamcinolone acetonide, diflorasone diacetate or betamethasone valerate.)

Furthermore, although the invention has been described in detail with particular reference to a preferred embodiment, it will be understood variations and modifications can be effected within the scope of the following claims. Such modifications may include substituting elements or components which perform substantially the same function in substantially the same way to achieve substantially the same result for those described herein.

What is claimed is:

1. A method of manufacturing a medical electrical lead comprising the steps of:
   assembling a lead;
   mixing a very slightly soluble in water steroid with an organic solvent to form a solution;
   applying the solution to the lead; and
   drying the solution on the lead to drive off the organic solvent.

2. The method of manufacturing medical electrical lead according to claim 1 wherein the step of mixing a very slightly soluble in water steroid with an organic solvent to form a solution comprises the steps of dissolving beclomethasone dipropionate anhydrous in acetone.

3. The method of manufacturing a medical electrical lead according to claim 2 wherein the step of dissolving beclomethasone dipropionate anhydrous into acetone comprises forming a saturated solution of beclomethasone dipropionate anhydrous in acetone.

4. The method of manufacturing medical electrical lead according to claim 1 wherein the step of mixing a very slightly soluble in water steroid with an organic solvent to form a solution comprises mixing a very slightly soluble in water steroid with an organic solvent to form a saturated solution.

5. The method of manufacturing medical electrical lead according to claim 1 wherein the step of applying the solution to the lead comprises applying a saturated solution of beclomethasone dipropionate anhydrous in acetone.

6. A method of manufacturing a medical electrical lead comprising the steps of:
   assembling a lead, the lead having an electrode;
   forming a saturated solution of a steroid which is at least very slightly soluble in water and a solvent;
   applying the saturated solution to the electrode; and drying the saturated solution on the electrode to drive off the organic solvent but not the steroid from the electrode.

7. The method of manufacturing medical electrical lead according to claim 6 wherein the step of applying the saturated solution to the electrode comprises applying the saturated solution to an exterior surface of the electrode.

8. The method of manufacturing medical electrical lead according to claim 6 wherein the step of forming a saturated solution of a steroid which is at least very slightly soluble in water and a solvent comprises the steps of dissolving beclomethasone dipropionate anhydrous into acetone.

9. The method of manufacturing medical electrical lead according to claim 8 wherein the step of applying the saturated solution to the electrode comprises applying a saturated solution of beclomethasone dipropionate anhydrous in acetone.

10. The method of manufacturing medical electrical lead according to claim 6 wherein the step of mixing a very slightly soluble in water steroid with an organic solvent to form a solution comprises mixing a very slightly soluble in water steroid with an organic solvent to form a saturated solution.

11. A method of manufacturing a medical electrical lead comprising the steps of:

assembling a lead, the lead having an electrode;

forming a saturated solution of a drug which is at least very slightly soluble in water and a solvent;

depositing on the surface of the electrode the saturated solution to the electrode; and driving off the solvent from the saturated solution deposited on the electrode such that the drug remains on the surface of the electrode.

12. The method of manufacturing medical electrical lead according to claim 11 wherein the step of driving off the solvent from the saturated solution deposited on the electrode such that the drug remains on the surface of the electrode comprises drying the saturated solution.

13. The method of manufacturing medical electrical lead according to claim 11 wherein the step of forming a saturated solution of a drug which is at least very slightly soluble in water and a solvent comprises forming a saturated solution of a steroid which is at least very slightly soluble in water and a solvent.

14. The method of manufacturing medical electrical lead according to claim 11 wherein the step of forming a saturated solution of a steroid which is at least very slightly soluble in water and a solvent comprises the steps of dissolving beclomethasone dipropionate anhydrous into acetone.

15. The method of manufacturing medical electrical lead according to claim 14 wherein the step of applying the saturated solution to the electrode comprises applying a saturated solution of beclomethasone dipropionate anhydrous in acetone.

16. The method of manufacturing medical electrical lead according to claim 11 wherein the step of mixing a very slightly soluble in water drug with an organic solvent to form a solution comprises mixing a very slightly soluble in water steroid with an organic solvent to form a saturated solution.

* * * * *